(12) United States Patent
Cai et al.

(10) Patent No.: US 8,188,287 B2
(45) Date of Patent: May 29, 2012

(54) PIPERIDYL ACRYLAMIDE ANTAGONISTS OF CCR2

(75) Inventors: Chaozhong Cai, North Wales, PA (US); Zhihua Sui, Exton, PA (US)

(73) Assignee: Janssen Pharmaceutica N.V. (BE)

( * ) Notice: Subject to any disclaimer, the term of this patent is extended or adjusted under 35 U.S.C. 154(b) by 448 days.

(21) Appl. No.: 12/487,742

(22) Filed: Jun. 19, 2009

(65) Prior Publication Data

US 2009/0318498 A1    Dec. 24, 2009

Related U.S. Application Data

(60) Provisional application No. 61/074,837, filed on Jun. 23, 2008.

(51) Int. Cl.
  *C07D 401/00* (2006.01)
  *A61K 31/445* (2006.01)
(52) U.S. Cl. .................. 546/187; 514/316
(58) Field of Classification Search ............ 546/187; 514/316
  See application file for complete search history.

(56) References Cited

U.S. PATENT DOCUMENTS

2006/0069123 A1    3/2006    Xia et al.

FOREIGN PATENT DOCUMENTS

WO    WO 2007/130712    11/2007

OTHER PUBLICATIONS

Dawson, et al, "Targeting Monocyte Chemoattractant Protein-1 Signalling in Disease", Expert Opin. Ther. Targets, 2003, vol. 7(1), pp. 35-48.
Seebach, et al, "Safe One-Pot Carbon-Carbon Bond Formation with Lithiated Nitrosamines Including Denitrosation by Sequential Reduction with Lithium a Aluminium Hydride and Raney-Nickel", Synthesis, 1979, vol. 6, pp. 423-424.
Gdaniec, et al., "Conformation and Stereodynamics of N,N-Dinitroso-2,4,6,8-tetraaryl-3,7-diazabicyclo [3.3.1] nonanes", J. Org. Chem., 1997 vol. 62, pp. 5619-5622.
Abdel-Magid, et al., "Reductive Amination of Aldehydes and Ketones with Sodium Triacetoxyborohydride. Studies on Direct and Indirect Reductive Amination Procedures", J. Org. Chem, 1996, vol. 61, pp. 3849-3862.
Chan, et al., "1,5-BIS (Trimethylsiloxy)-1,5-Dimethoxy-1-4-Pentadienes. Cyclopropance Synthesis Via Intramolecular Coupling", Tetrahedron Letters, 1982 vol. 23, No. 8, pp. 799-802.
Rollins, "Monocyte chemoattractant protein 1: a potential regulator of monocyte recruitment in inflammatory disease", 89Mol. Med. Today, 1996 vol. 2, pp. 198.
Das, B. et al. "A Highly Chemoselective Boc Protection of Amines using Sulfonic-Acid-Functionalized Silica As an Efficient Heterogeneous Recyclable Catalyst", Tetrahedron Lett. 2006, 47, 7551-7556.
Ingersoll, A. W. et. al., "Hippuric Acid", Organic Syntheses 1932, XII, vol. 12. pp. 40.
Xia M, Sui Z, "Recent Developments in CCR2 Antagonists", *Expert Opin. Ther. Patents*, 2009, 19(3), 295-303.

*Primary Examiner* — Janet Andres
*Assistant Examiner* — John Mabry
(74) *Attorney, Agent, or Firm* — Mary A. Appollina

(57) ABSTRACT

The present invention comprises compounds of Formula I.

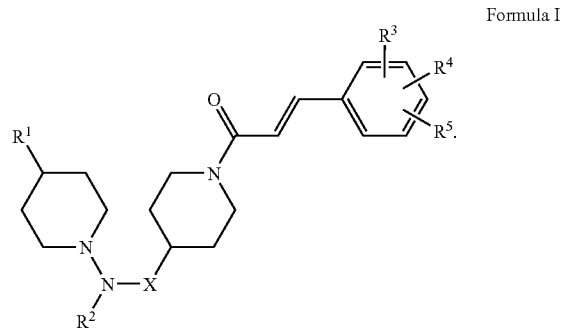

Formula I wherein: $R^1$, $R^2$, $R^3$, $R^4$, $R^5$ and X are as defined in the specification. The invention also comprises a method of treating or ameliorating a syndrome, disorder or disease, wherein said syndrome, disorder or disease is uveitis, including acute, recurring or chronic uveitis. The invention also comprises a method of inhibiting CCR2 activity in a mammal by administration of a therapeutically effective amount of at least one compound of Formula I.

9 Claims, No Drawings

PIPERIDYL ACRYLAMIDE ANTAGONISTS OF CCR2

CROSS-REFERENCE TO RELATED APPLICATIONS

This application claims priority from U.S. Provisional Applications Ser. No. 61/074,837 filed Jun. 23, 2008, the contents of each of which are hereby incorporated by reference in their entirety.

FIELD OF THE INVENTION

The invention is directed to substituted dipiperidine compounds, which are antagonists to the chemoattractant cytokine receptor 2 (CCR2), pharmaceutical compositions, and methods for use thereof. More particularly, the CCR2 antagonists are substituted piperidyl acrylamide compounds useful for preventing, treating or ameliorating a CCR2 mediated inflammatory syndrome, disorder or disease.

BACKGROUND OF THE INVENTION

CCR2 is a member of the GPCR family of receptors, as are all known chemokine receptors, and are expressed by monocytes and memory T-lymphocytes. The CCR2 signaling cascade involves activation of phospholipases (PLCβ2), protein kinases (PKC), and lipid kinases (PI-3 kinase).

Chemoattractant cytokines (i.e., chemokines) are relatively small proteins (8-10 kD), which stimulate the migration of cells. The chemokine family is divided into four subfamilies based on the number of amino acid residues between the first and second highly conserved cysteines.

Monocyte chemotactic protein-1 (MCP-1) is a member of the CC chemokine subfamily (wherein CC represents the subfamily having adjacent first and second cysteines) and binds to the cell-surface chemokine receptor 2 (CCR2). MCP-1 is a potent chemotactic factor, which, after binding to CCR2, mediates monocyte and lymphocyte migration (i.e., chemotaxis) toward a site of inflammation. MCP-1 is also expressed by cardiac muscle cells, blood vessel endothelial cells, fibroblasts, chondrocytes, smooth muscle cells, mesangial cells, alveolar cells, T-lymphocytes, marcophages, and the like. After monocytes enter the inflammatory tissue and differentiate into macrophages, monocyte differentiation provides a secondary source of several proinflammatory modulators, including tumor necrosis factor-α (TNF-α), interleukin-1 (IL-1), IL-8 (a member of the CXC chemokine subfamily, wherein CXC represents one amino acid residue between the first and second cysteines), IL-12, arachidonic acid metabolites (e.g., $PGE_2$ and $LTB_4$), oxygen-derived free radicals, matrix metalloproteinases, and complement components.

Animal model studies of chronic inflammatory diseases have demonstrated that inhibition of binding between MCP-1 and CCR2 by an antagonist suppresses the inflammatory response. The interaction between MCP-1 and CCR2 has been implicated (see Rollins B J, Monocyte chemoattractant protein 1: a potential regulator of monocyte recruitment in inflammatory disease, *Mol. Med. Today*, 1996, 2:198; and Dawson J, et al., Targeting monocyte chemoattractant protein-1 signaling in disease, *Expert Opin. Ther. Targets*, Feb. 7, 2003 (1):35-48) in inflammatory disease pathologies such as psoriasis, uveitis, atherosclerosis, rheumatoid arthritis (RA), multiple sclerosis, Crohn's Disease, nephritis, organ allograft rejection, fibroid lung, renal insufficiency, diabetes and diabetic complications, diabetic nephropathy, diabetic retinopathy, diabetic retinitis, diabetic microangiopathy, tuberculosis, sarcoidosis, invasive *staphylococcia*, inflammation after cataract surgery, allergic rhinitis, allergic conjunctivitis, chronic urticaria, Chronic Obstructive Pulmonary Disease (COPD), allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, and stomach.

Monocyte migration is inhibited by MCP-1 antagonists (either antibodies or soluble, inactive fragments of MCP-1), which have been shown to inhibit the development of arthritis, asthma, and uveitis. Both MCP-1 and CCR2 knockout (KO) mice have demonstrated that monocyte infiltration into inflammatory lesions is significantly decreased. In addition, such KO mice are resistant to the development of experimental allergic encephalomyelitis (EAE, a model of human MS), cockroach allergen-induced asthma, atherosclerosis, and uveitis. Rheumatoid arthritis and Crohn's Disease patients have improved during treatment with TNF-α antagonists (e.g., monoclonal antibodies and soluble receptors) at dose levels correlated with decreases in MCP-1 expression and the number of infiltrating macrophages. MCP-1 has been implicated in the pathogenesis of seasonal and chronic allergic rhinitis, having been found in the nasal mucosa of most patients with dust mite allergies. MCP-1 has also been found to induce histamine release from basophils in vitro. During allergic conditions, both allergens and histamines have been shown to trigger (i.e., to up-regulate) the expression of MCP-1 and other chemokines in the nasal mucosa of people with allergic rhinitis, suggesting the presence of a positive feedback loop in such patients.

There remains a need for small molecule CCR2 antagonists for preventing, treating or ameliorating a CCR2 mediated inflammatory syndrome, disorder or disease resulting from MCP-1 induced monocyte and lymphocyte migration to a site of inflammation. All documents cited herein are incorporated by reference.

SUMMARY OF THE INVENTION

The present invention comprises compounds of Formula I.

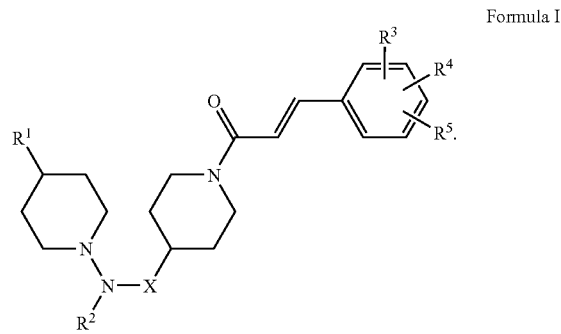

Formula I wherein:

$R^1$ is phenyl, naphthyl, heteroaryl, or partially saturated benzofused heteroaryl wherein the phenyl, naphthyl, heteroaryl, or partially saturated benzofused heteroaryl may be optionally substituted with up to three substituents selected from the group consisting of —F, —Cl, —CF$_3$, —CN, —C$_{(1-4)}$alkyl, —C$_{(1-4)}$alkylOH, —C$_{(1-4)}$alkylNH$_2$, —C$_{(1-4)}$alkylNHC$_{(1-4)}$alkyl, —C$_{(1-4)}$alkylN(C$_{(1-4)}$alkyl)$_2$, —NO$_2$, —NHC$_{(1-4)}$alkyl, —CONHC$_{(1-4)}$alkyl, —SO$_2$NHC$_{(1-4)}$alkyl, —OC$_{(1-4)}$alkyl, —NH$_2$, —CONH$_2$, —SO$_2$NH$_2$, —NHCOCH$_3$, and —OH;

R$^2$ is H, or —C$_{(1-4)}$alkyl, —C$_{(1-4)}$alkyl-OH, wherein said —C$_{(1-4)}$alkyl and said —C$_{(1-4)}$alkyl-OH are optionally substituted with —OH, —NH$_2$, —F, —Cl, heteroaryl (including imidazol-2-yl), or phenyl;

X is a direct bond, or CHCO$_2$H;

R$^3$ is —F, —Cl, —CF$_3$, —CN, —C$_{(1-4)}$alkyl, —C$_{(1-4)}$alkylOH, —C$_{(1-4)}$alkylNH$_2$, —C$_{(1-4)}$alkylNHC$_{(1-4)}$alkyl, —C$_{(1-4)}$alkylN(C$_{(1-4)}$alkyl)$_2$, —NO$_2$, —NHC$_{(1-4)}$alkyl, —CONHC$_{(1-4)}$alkyl, —SO$_2$NHC$_{(1-4)}$alkyl, —OC$_{(1-4)}$alkyl, —NH$_2$, —CONH$_2$, —SO$_2$NH$_2$, —NHCOCH$_3$, or —OH;

R$^4$ is —F, —Cl, —OCH$_3$, or may be taken together with an adjacent R$^3$ to form a methylidene acetal; and R$^5$ is —F, Cl, or —OCH$_3$;

and solvates, hydrates, and pharmaceutically acceptable salts thereof.

DETAILED DESCRIPTION OF THE INVENTION

The present invention comprises compounds of Formula I.

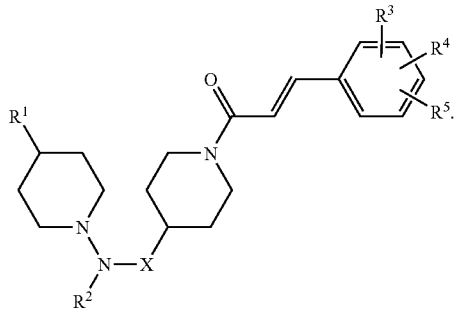

Formula I wherein:

R$^1$ is phenyl, naphthyl, heteroaryl, or partially saturated benzofused heteroaryl, wherein the phenyl, naphthyl, heteroaryl, or partially saturated benzofused heteroaryl may be optionally substituted with up to three substituents selected from the group consisting of —F, —Cl, —CF$_3$, —CN, —C$_{(1-4)}$alkyl, —C$_{(1-4)}$alkylOH, —C$_{(1-4)}$alkylNH$_2$, —C$_{(1-4)}$alkylNHC$_{(1-4)}$alkyl,
—C$_{(1-4)}$alkylN(C$_{(1-4)}$alkyl)$_2$, —NO$_2$, —NHC$_{(1-4)}$alkyl, —CONHC$_{(1-4)}$alkyl, —SO$_2$NHC$_{(1-4)}$alkyl, —OC$_{(1-4)}$alkyl, —NH$_2$, —CONH$_2$, —SO$_2$NH$_2$, —NHCOCH$_3$, and —OH;

R$^2$ is H, —C$_{(1-4)}$alkyl, or —C$_{(1-4)}$alkyl-OH, wherein said —C$_{(1-4)}$alkyl and said —C$_{(1-4)}$alkyl-OH are optionally substituted with —OH, —NH$_2$, —F, —Cl, heteroaryl (including imidazol-2-yl), or phenyl;

X is a direct bond, or CHCO$_2$H;

R$^3$ is —F, —Cl, —CF$_3$, —CN, —C$_{(1-4)}$alkyl, —C$_{(1-4)}$alkylOH, —C$_{(1-4)}$alkylNH$_2$, —C$_{(1-4)}$alkylNHC$_{(1-4)}$alkyl, —C$_{(1-4)}$alkylN(C$_{(1-4)}$alkyl)$_2$, —NO$_2$, —NHC$_{(1-4)}$alkyl, —CONHC$_{(1-4)}$alkyl, —SO$_2$NHC$_{(1-4)}$alkyl, —OC$_{(1-4)}$alkyl, —NH$_2$, —CONH$_2$, —SO$_2$NH$_2$, —NHCOCH$_3$, or —OH;

R$^4$ is —F, —Cl, —OCH$_3$, or may be taken together with an adjacent R$^3$ to form a methylidene acetal; and R$^5$ is —F, Cl, or —OCH$_3$;

and solvates, hydrates, and pharmaceutically acceptable salts thereof.

In another embodiment of the invention:

R$^1$ is

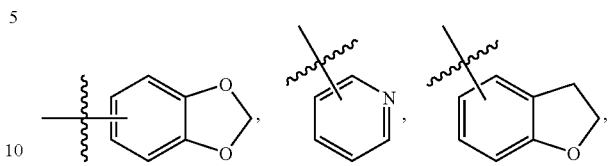

or indolyl any of which may be optionally substituted with up to three substituents selected from the group consisting of —F, —Cl, —CF$_3$, —CN, —C$_{(1-4)}$alkyl, —C$_{(1-4)}$alkylOH, —C$_{(1-4)}$alkylNH$_2$, —C$_{(1-4)}$alkylNHC$_{(1-4)}$alkyl, —C$_{(1-4)}$alkylN(C$_{(1-4)}$alkyl)$_2$, —NO$_2$, —NHC$_{(1-4)}$alkyl, —CONHC$_{(1-4)}$alkyl, —SO$_2$NHC$_{(1-4)}$alkyl, —OC$_{(1-4)}$alkyl, —NH$_2$, —CONH$_2$, —SO$_2$NH$_2$, —NHCOCH$_3$, and —OH;

R$^2$ is H,

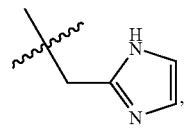

—C$_{(1-4)}$alkyl, or —C$_{(1-4)}$alkyl-OH, wherein said —C$_{(1-4)}$alkyl and said —C$_{(1-4)}$alkyl-OH are optionally substituted with —OH, —NH$_2$, —F, —Cl, or phenyl;

X is a direct bond or CHCO$_2$H;

R$^3$ is —F, —Cl, —CF$_3$, —CN, —C$_{(1-4)}$alkyl, —C$_{(1-4)}$alkylOH, —C$_{(1-4)}$alkylNH$_2$, —C$_{(1-4)}$alkylNHC$_{(1-4)}$alkyl, —C$_{(1-4)}$alkylN(C$_{(1-4)}$alkyl)$_2$, —NO$_2$, —NHC$_{(1-4)}$alkyl, —OC$_{(1-4)}$alkyl, —NH$_2$, or —OH;

R$^4$ is —F, —Cl, —OCH$_3$, or may be taken together with an adjacent R3 to form a methylidene acetal; and R$^5$ is —F, Cl, or —OCH$_3$;

and solvates, hydrates, and pharmaceutically acceptable salts thereof.

In another embodiment of the invention:

R$^1$ is

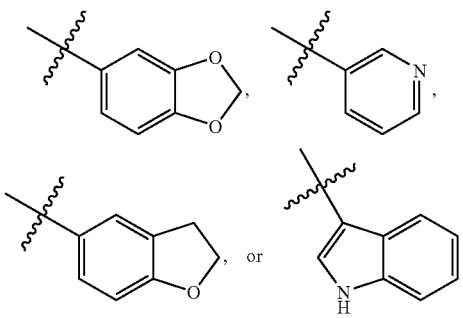

any of which may be optionally substituted with up to three substituents selected from the group consisting of —F, —Cl, —CF$_3$, —CN, —OH, —OC$_{(1-4)}$alkyl, —C$_{(1-4)}$alkyl, and —C$_{(1-4)}$alkylOH;

R² is H,

[structure: imidazolylmethyl]

—C₍₁₋₄₎alkyl, or —C₍₁₋₄₎alkyl-OH, wherein said —C₍₁₋₄₎alkyl and said —C₍₁₋₄₎alkyl-OH are optionally substituted with —OH, —NH₂, —F, or —Cl;
X is a direct bond or CHCO₂H;
R³ is —F, Cl, or —OCH₃;
R⁴ is —F, —Cl, —OCH₃, or may be taken together with an adjacent R³ to form a methylidene acetal; and
R⁵ is —F, Cl, or —OCH₃;
and solvates, hydrates, and pharmaceutically acceptable salts thereof.

In another embodiment of the invention:
R¹ is

[structures: benzodioxole, pyridine, dihydrobenzofuran, or indole]

R² is H,

[structure: imidazolylmethyl]

—C₍₁₋₄₎alkyl, or —C₍₁₋₄₎alkyl-OH, wherein said —C₍₁₋₄₎alkyl-OH is optionally substituted with —OH;
X is a direct bond or CHCO₂H;
R³ is —F, Cl, or —OCH₃;
R⁴ is —F, Cl, or —OCH₃; and
R⁵ is —F, Cl, or —OCH₃;
and solvates, hydrates, and pharmaceutically acceptable salts thereof.

In another embodiment of the invention:
R¹ is

[structure: indole]

R² is H, C₍₁₋₄₎alkyl, dihydroxypropyl, or

[structure: imidazolylmethyl]

X is a direct bond or CHCO₂H;
R³ is F;
R⁴ is F; and
R⁵ is F;
and solvates, hydrates, and pharmaceutically acceptable salts thereof.

Another embodiment of the invention is a compound selected from the group consisting of:

[six chemical structures shown]

; and

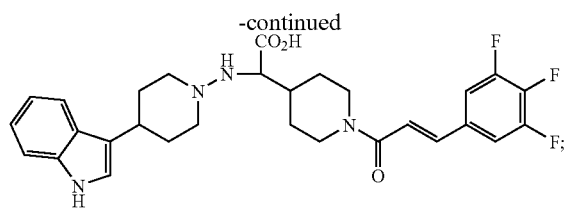

and solvates, hydrates, and pharmaceutically acceptable salts thereof.

Another embodiment of the invention is a pharmaceutical composition, comprising a compound of Formula I and a pharmaceutically acceptable carrier.

Another embodiment of the invention is a pharmaceutical composition, comprising a compound listed in the Examples section of this specification and a pharmaceutically acceptable carrier.

The present invention also provides a method for preventing, treating or ameliorating a CCR2 mediated inflammatory syndrome, disorder or disease comprising administering to a subject in need thereof an effective amount of a compound of Formula I or a form, composition or medicament thereof.

The present invention also provides a method for preventing, treating or ameliorating a CCR2 mediated inflammatory syndrome, disorder or disease wherein the syndrome, disorder or disease is associated with elevated MCP-1 expression or MCP-1 overexpression, or is an inflammatory condition that accompanies syndromes, disorders or diseases associated with elevated MCP-1 expression or MCP-1 overexpression comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive *staphyloccocia*, inflammation after cataract surgery, allergic rhinitis, allergic conjunctivitis, chronic urticaria, asthma, allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: ophthalmic disorders, rheumatoid arthritis, psoriasis, psoriatic arthritis, atopic dermatitis, chronic obstructive pulmonary disease, allergic rhinitis, asthma, allergic asthma, and periodontal diseases comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: uveitis, allergic conjunctivitis, and periodontal disease selected from the group consisting of periodonitis, gingivitis and gum disease comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: acute uveitis, recurring uveitis, chronic uveitis, allergic conjunctivitis, rheumatoid arthritis, psoriasis, psoriatic arthritis, atopic dermatitis, chronic obstructive pulmonary disease, allergic rhinitis, asthma, allergic asthma, periodonitis, gingivitis or gum disease comprising administering to a subject in need thereof an effective amount of the compound of claim 1 or composition or medicament thereof.

The present invention provides a method of treating or ameliorating a syndrome, disorder or disease, in a subject in need thereof comprising administering to the subject an effective amount of the compound of claim 1 or composition or medicament thereof in a combination therapy with one or more anti-inflammatory agents, anti-infective agents or immunosuppressive agents, wherein said syndrome, disorder or disease is selected from the group consisting of: uveitis, allergic conjunctivitis, and periodontal disease selected from the group consisting of periodonitis, gingivitis and gum disease.

The present invention provides a method of treating or ameliorating a syndrome, disorder or disease, wherein said syndrome, disorder or disease is uveitis, including acute, recurring or chronic uveitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is uveitis, including anterior uveitis, intermediate uveitis, posterior uveitis or panuveitis comprising administering to a subject in need thereof an effective amount of a compound of Formula I or a form, composition or medicament thereof.

The invention also relates to methods of inhibiting CCR2 activity in a mammal by administration of an effective amount of at least one compound of Formula I.

Definitions

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "heteroaryl" refers to 5- to 7-membered mono- or 8- to 10-membered bicyclic aromatic ring systems, any ring of which may consist of from one to four heteroatoms selected from N, O or S where the nitrogen and sulfur atoms can exist in any allowed oxidation state. Examples include, but are not limited to, benzimidazolyl, benzofuryl, benzothiazolyl, benzothienyl, benzoxazolyl, furyl, imidazolyl, indolyl, isothiazolyl, isoxazolyl, oxazolyl, pyrazinyl, pyrazolyl, pyridyl, pyrimidinyl, pyrrolyl, quinolinyl, thiazolyl and thienyl.

The term "partially saturated benzofused heteroaryl" refers to an 8- to 10-membered bicyclic heteroaryl group as defined above wherein one of the rings is saturated by one or more hydrogen atoms. Examples include, but are not limited to, dihydrobenzofuryl, benzodioxanyl, benzodioxolyl, and methylenedioxyphenyl.

The term "heteroatom" refers to a nitrogen atom, an oxygen atom or a sulfur atom wherein the nitrogen and sulfur atoms can exist in any allowed oxidation states.

The term "methylidene acetal" refers to the functional group

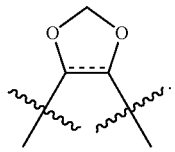

For use in medicines, the salts of the compounds of this invention refer to non-toxic "pharmaceutically acceptable salts." FDA approved pharmaceutically acceptable salt forms (Ref. International J. Pharm. 1986, 33, 201-217; J. Pharm. Sci., 1977, January, 66(1), p1) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethylpropane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine (TEA) or zinc.

Methods of Use

The present invention is directed to a method for preventing, treating or ameliorating a CCR2 mediated inflammatory syndrome, disorder or disease comprising administering to a subject in need thereof an effective amount of a compound of Formula (I) or a form, composition or medicament thereof.

The term "administering" with respect to the methods of the invention, means a method for therapeutically or prophylactically preventing, treating or ameliorating a syndrome, disorder or disease as described herein by using a compound of Formula (I) or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be animal, typically a mammal, typically a human, which has been the object of treatment, observation or experiment and is at risk of (or susceptible to) developing a syndrome, disorder or disease that is associated with elevated MCP-1 expression or MCP-1 overexpression, or a patient with an inflammatory condition that accompanies syndromes, disorders or diseases associated with elevated MCP-1 expression or MCP-1 overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

The term "uveitis" generically refers to any inflammatory disease involving the eye. Uveitis can be divided into clinically distinct subtypes based on the part of the eye in which the inflammation is present (percentages correspond to patients known to fit these categories): anterior (51%), intermediate (13%), posterior (20%), or panuveitis (16%) and, according to the course of the disease, as either acute (16%), recurring (26%), or chronic (58%). Those with anterior uveitis (·19%) eventually develop irreparable vision damage despite aggressive treatment such as unilateral blindness (9%), bilateral blindness (2%), or unilateral or bilateral vision impairment (8%). Most cases of uveitis are idiopathic, but known causes include infection (e.g., toxoplasmosis, cytomegalovirus, and the like) or development as a component of a systemic inflammatory and/or autoimmune disorder (e.g., juvenile RA, HLA-B27 associated spondyloarthropathies, sarcoidosis, and the like). (HLA-B27: Human Leukocyte Antigen B*27—is a class I surface antigen encoded by the B locus in the major histocompatibility complex (MHC) on chromosome 6 and presents micobial antigens to T cells. HLA-B27 is strongly associated with a certain set of autoimmune diseases referred to as the seronegative spondyloarthropathies.)

When employed as CCR2 inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in the Examples or Formula I for use as a medicament.

In another embodiment, the invention relates to the use of a compound as described in the Examples or Formula I for the preparation of a medicament for the treatment of a disease associated with an elevated or inappropriate CCR2 activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

General Reaction Scheme

Representative compounds of the present invention can be synthesized in accordance with the general synthetic methods described below. Compounds of Formula I can be prepared by methods known to those who are skilled in the art. The following reaction schemes are only meant to represent examples of the invention and are in no way meant to be a limit of the invention.

Scheme A

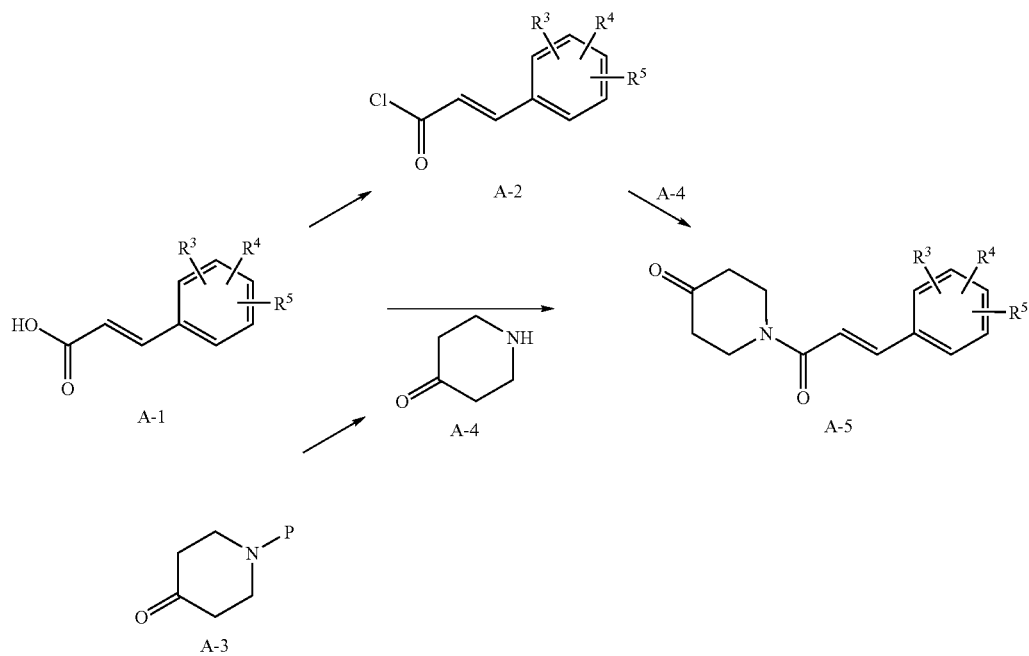

Wherein P is Boc, or Cbz

Acrylic acids of the formula A-1, wherein $R^3$, $R^4$ and $R^5$ are as defined in Formula I, can be coupled with Compound A-4 using a coupling agent such as EDCI (1-ethyl-3-(3'-dimethylaminopropyl)carbodiimide) and an additive such as HOBt (1-hydroxybenzotriazole) to provide a compound of formula A-5. Compound A-4 can be obtained by deprotection of the commercially available A-3, using either acidic conditions in the case of Boc

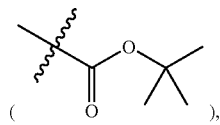

or hydrogenation in the case of Cbz

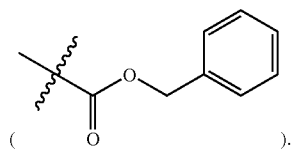

Acrylic acids of formula A-1 are either commercially available, or readily synthesized by known methods. (Adams, R.; Mathieu, Jean. *J. Am. Chem. Soc.* 1948, 70, 2120-2122.)

Alternatively, an acrylic acid of the formula A-1 may react with a suitable source of chlorine such as thionyl chloride, $PCl_3$, $PCl_5$, or oxalyl chloride; in an organic solvent such as DCM (dichloromethane); preferably at reflux, to yield the corresponding acid chloride A-2. Reaction of A-2 with A-4 in the presence of an organic base such TEA (triethylamine), or DIPEA (diisopropylethylamine) in an organic solvent such as DCM yields the amide A-5. Amides of formula A-5 may be converted into compounds of Formula I as shown in General Scheme D.

Intermediate B-7 may be prepared according to the procedure outlined in Scheme B. Compounds of formula B-7 are used for synthesis compounds of formula I wherein $R^1$ is indolyl or pyrrole-fused heteroaryl.

Scheme B

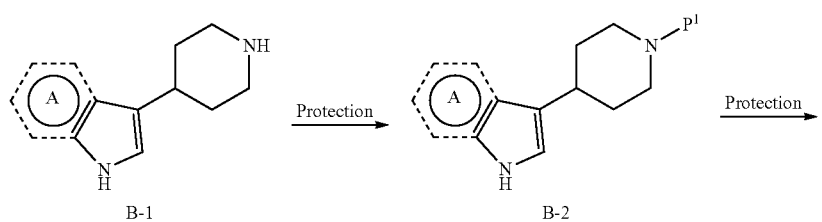

-continued

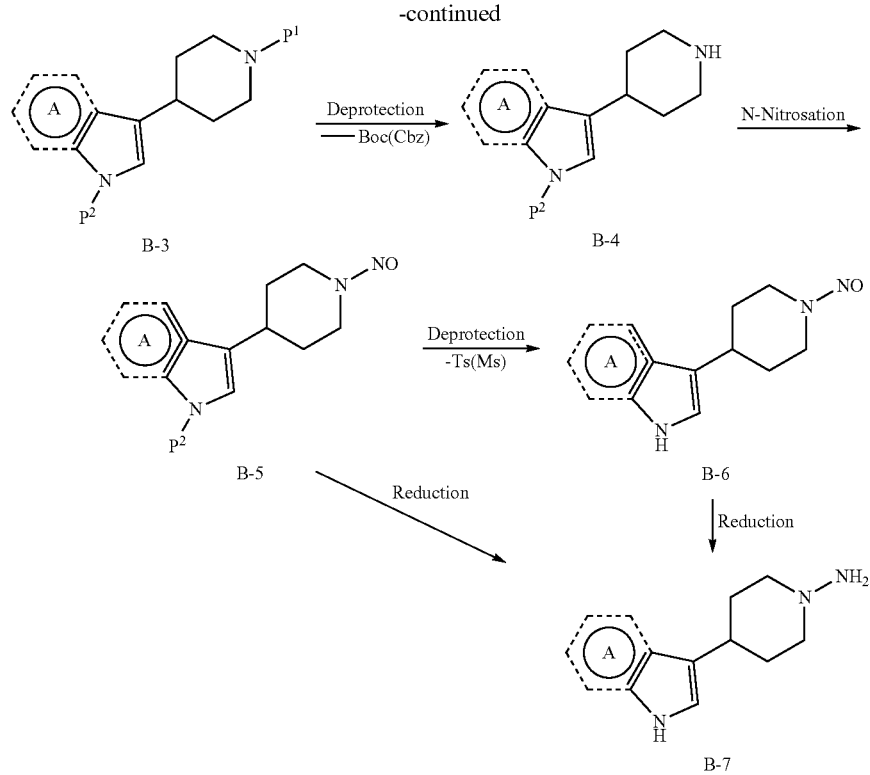

wherein

⟨A⟩ is phenyl, or heteroaryl; $P^1$ is Boc, or Cbz; and $P^2$ is mesylate, or tosylate.

Piperidine B-1, available either commercially or prepared by reported protocols in the scientific literature, may be protected by Boc (or Cbz and other carbamates) using procedures described in Green, T. W., Wuts, P. G. M., "Protective Groups in Organic Synthesis", Wiley-Interscience, and references therein to give a compound of formula B-2. The aromatic nitrogen of the compound of formula B-2 may subsequently be protected using a tosyl or mesyl group to afford B-3. One skilled in the art will recognize that the protecting group on the aromatic nitrogen should stay during the process of removal of the protecting group (such as Boc, Cbz and the like) on the nitrogen of piperidine.

The protecting group on nitrogen of piperidine in the compound of formula B-3 may be selectively removed by known methods. For example, treatment of a solution of Compound B-3 in an organic solvent such as DCM, dioxane and the like, with an organic or inorganic acid such as TFA (trifluoroacetic acid) or HCl and the like, in the case of Boc; or hydrogenation in the presence of a catalyst such as palladium and the like in an organic solvent such as methanol, THF (tetrahydrofuran) and the like, in the case of Cbz, gave a compound of formula B-4.

The compound of formula B-4 may be nitrosated with nitrite salt (such as $NaNO_2$, or $KNO_2$) in the presence of a protic acid (such as HCl) to afford B-5 (Maria, G., et. al., *J. Org. Chem.*, 1997, 62, 5619-5622).

Removal of the protecting group on the aromatic nitrogen by known methods yields B-6 (Green, T. W., Wuts, P. G. M., "Protective Groups in Organic Synthesis", Wiley-Interscience, and references therein). Reduction of nitroso of B-6 with a reducing agent such as $LiAlH_4$ in a organic solvent such as diethyl ether, or THF, gives the compound of formula B-7 (Seebach, D., et. al., *Synthesis*, 1979, 6, 423-424).

Alternately, one skilled in the art may convert the compound of formula B-5 directly to the compound of formula B-7 in one step. For example, a solution of B-5 in a organic solvent such as diethyl ether, or THF, may be treated with a reducing agent such as $LiAlH_4$ at low temperature, such as 0° C., followed by reflux and workup, to afford the compound B-7.

Intermediate C-3 may be prepared according to the procedure outlined in Scheme C. Compounds of formula C-3 are used for synthesis of compounds of formula I wherein $R^1$ is neither indolyl nor pyrrole-fused heteroaryl.

Scheme C

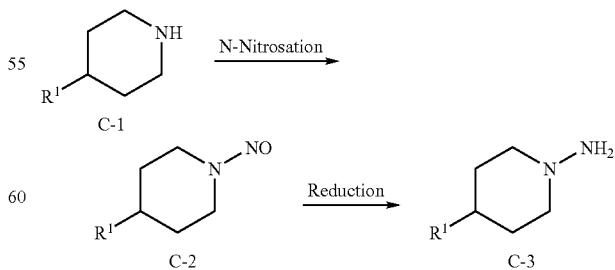

A 4-substituted piperidine of the formula C-1, available either commercially or prepared by reported protocols in the scientific literature, may be nitrosated to the corresponding compound of formula C-2 using a nitrite salt (such as NaNO$_2$, or KNO$_2$) in the presence of a protic acid (such as HCl) to afford C-2 (Maria, G., et. al., *J. Org. Chem.,* 1997, 62, 5619-5622). Subsequent reduction of the nitroso-piperidine of formula C-2 with a reducing agent such as LiAlH$_4$ in a organic solvent such as diethyl ether, or THF, gives the compound of formula C-3 (Seebach, D., et. al., *Synthesis,* 1979, 6, 423-424).

The target compound (I-a) (representative of compounds of the formula I wherein X is a direct bond) may be prepared according to the process outlined in Scheme D below:

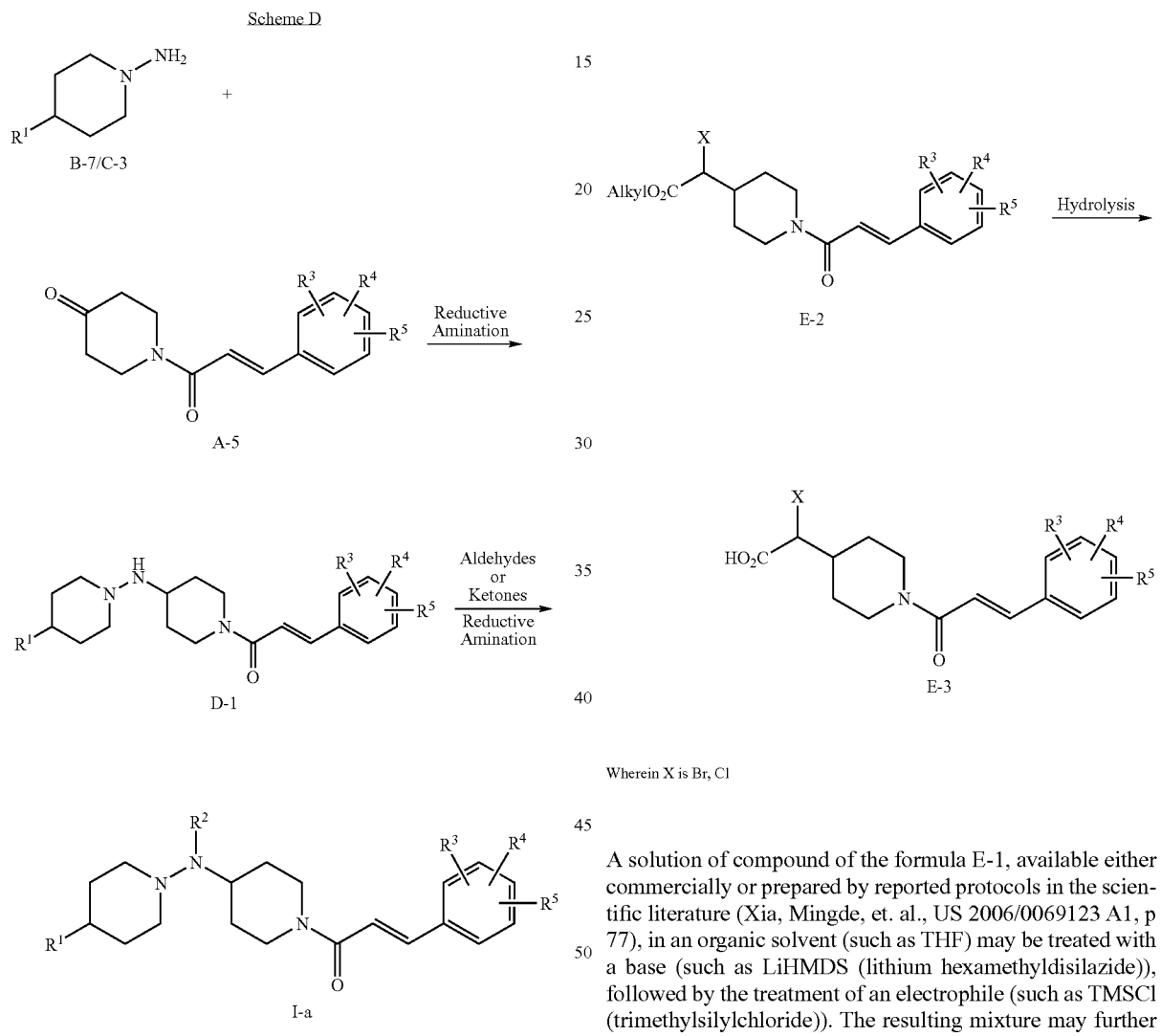

A compound of formula B-7 or C-3 may be reacted with Compound A-5 in a solvent or mixture of solvents such as DCM, DCE (dichloroethane), or THF, in the presence of a hydride source, such as sodium borohydride or sodium triacetoxyborohydride (Abdel-Magid, Ahmed F., et. al., *J. Org. Chem.,* 1996, 61, 3849-3862), to provide a compound of formula D-1.

While D-1 is a compound of Formula I in which R$^2$ is H, it may be derivatized further. Reaction of D-1 with a suitable aldehyde or ketone in a solvent or mixture of solvents such as DCM, DCE, or THF in the presence of a hydride source, such as sodium triacetoxyborohydride or sodium borohydride, affords the target Compound I-a, wherein R$^2$ is not H.

A solution of compound of the formula E-1, available either commercially or prepared by reported protocols in the scientific literature (Xia, Mingde, et. al., US 2006/0069123 A1, p 77), in an organic solvent (such as THF) may be treated with a base (such as LiHMDS (lithium hexamethyldisilazide)), followed by the treatment of an electrophile (such as TMSCl (trimethylsilylchloride)). The resulting mixture may further be reacted with a halogenating reagent such as NBS (N-bromosuccinimide), NCS (N-chlorosuccinimide), or bromine, in an organic solvent such as THF to give the compound of formula E-2 where X is bromo or chloro (Chan, T. H., Wallace, I. H. M., *Tetrahedron Letters,* 1982, 23, 799-802).

A solution of the compound E-2 may be hydrolyzed by an aqueous reagent solution (such as LiOH in a solvent such as THF, methanol, or a mixture thereof) at about room temperature, then acidified (using an acid such as HCl) to generate the compound of formula E-3.

The target compound (I-b) (representative of compounds of the formula I wherein X is CHCOOH) may be prepared according to the process outlined in Scheme F below:

Scheme F

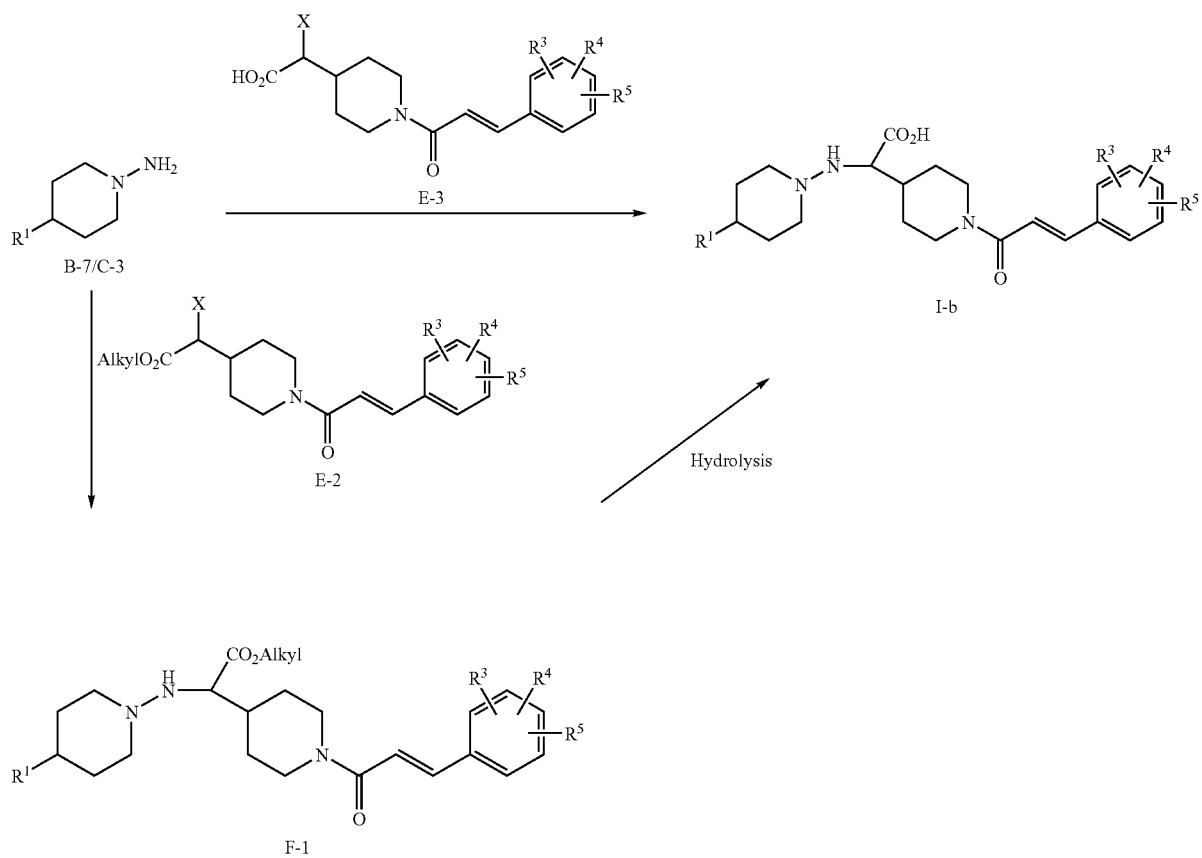

A solution (such as acetonitrile) of Compound B-7 or C-3 and a base, such as TEA (triethylamine) or DIPEA may be reacted, preferably at reflux, with a solution of compound E-3 in a solvent such as acetonitrile to provide a racemate Compound I-b. The racemate Compound I-b may be chromatographically separated using conventional resolution techniques known to those skilled in the art.

Alternatively, a solution (such as acetonitrile) of Compound B-7 or C-3 and a base, such as TEA or DIPEA may be reacted, preferably at reflux, with a solution of compound E-2 in a solvent such as acetonitrile to provide Compound F-1 as a racemic mixture. The compound of formula F-1 may be hydrolyzed under basic conditions (such as LiOH in a solvent such as THF, MeOH (methanol), or mixture thereof) at about room temperature, to give Compound I-b. The racemate Compound I-b may be chromatographically separated using conventional resolution techniques known to those skilled in the art.

SPECIFIC EXAMPLES

Example 1

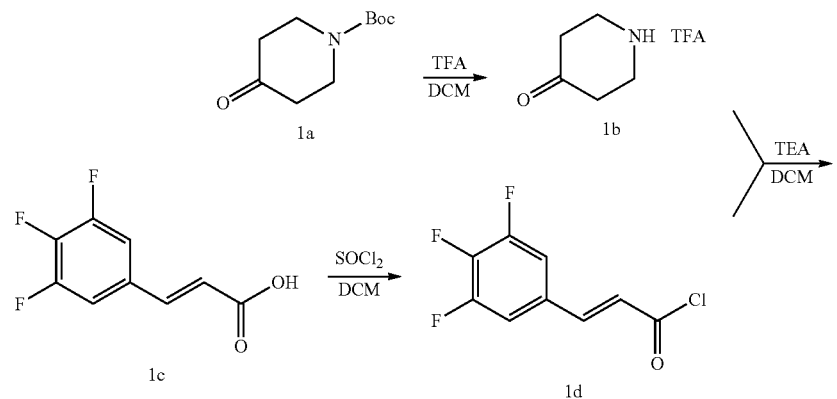

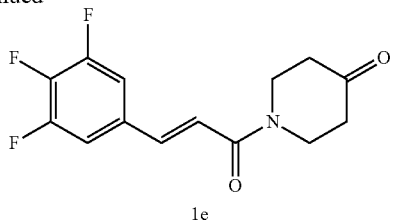

1e

A. Piperidin-4-one. To a solution of 4-oxo-piperidine-1-carboxylic acid tert-butyl ester (Compound 1a) (2.03 g, 10 mmol) in DCM (6 mL) was added TFA (6 mL) dropwise. The reaction was stirred at room temperature (rt) for 3 hours (h) and the volatiles were removed by evaporation. More DCM was added and evaporated again to provide compound 1b as a TFA salt. LC/MS: $C_5H_9NO$: m/z 100.0 (M+1).

B. 3-(3,4,5-Trifluoro-phenyl)-acryloyl chloride. A solution of 3-(3,4,5-trifluoro-phenyl)-acrylic acid (Compound 1c) (purchased from Aldrich) (2.02 g, 10 mmol) in DCM (20 mL) was stirred at rt for 5 min, followed by addition of $SOCl_2$ (1.5 mL, 20 mmol). The reaction mixture was heated at reflux for 2 h and evaporated to remove the volatiles. More DCM was added and evaporation again to provide the crude compound 1d for the next step without further purification.

C. 1-[3-(3,4,5-Trifluoro-phenyl)-acryloyl]-piperidin-4-one. To a solution of 1b (10 mmol), TEA (4.18 mL, 30 mmol) in DCM (28 mL) at 0° C. was added dropwise a solution of 1d (10 mmol) in DCM (4 mL). After being stirred at 0° C. for 15 minutes (min), the mixture was stirred at rt overnight. The reaction was quenched by addition of $H_2O$, the organic phase was washed with 1N HCl, $H_2O$ and dried over $Na_2SO_4$. Removal of solvents and purification by column chromatography (eluent: EtOAc (ethyl acetate)/hexanes, 1/1) gave the compound 1e. 2.08 g, 73%. $^1$H-NMR (400 MHz, $CDCl_3$): δ 7.56-7.60 (1H, d), 7.14-7.18 (2H, m), 6.84-6.88 (1H, d), 3.88-4.09 (4H, m), 2.55-2.58 (4H, t); LC/MS: $C_{14}H_{12}F_3NO_2$: m/z 284.3 (M+1).

Example 2

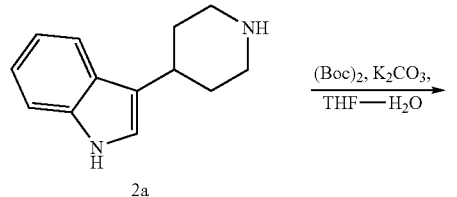

2a

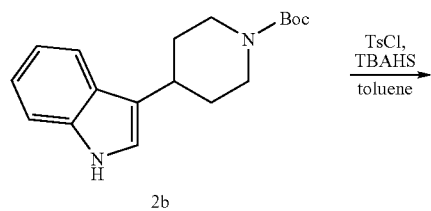

2b

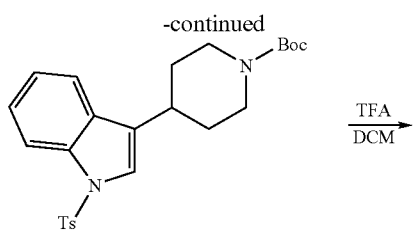

2c

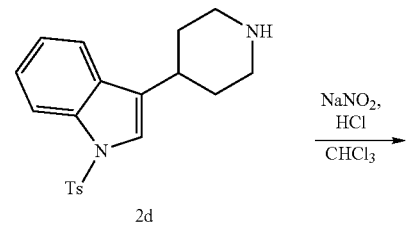

2d

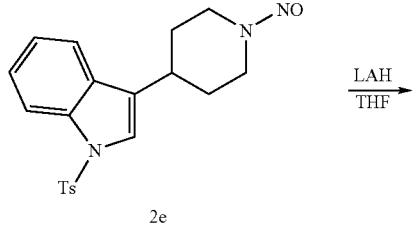

2e

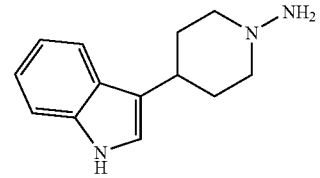

2f

A. 4-(1H-Indol-3-yl)-piperidine-1-carboxylic acid tert-butyl ester. A solution of 4-(3-indo)piperidine (compound 2a) (purchased from Tyger Scientific Inc.) (1.0 g, 5 mmol), di-tert-butyl dicarbonate (1.36 g, 6.25 mmol) and $K_2CO_3$ (2.19 g, 15.9 mmol) in THF (80 mL) and $H_2O$ (40 mL) was stirred at 60° C. for 22 h. Another batch of di-tert-butyl dicarbonate (1.1 g, 5 mmol) and $K_2CO_3$ (0.7 g, 5 mmol) was added and the mixture was stirred at 60° C. for another 5 h. After cooling to rt, the two phases were separated and the aqueous phase was extracted with EtOAc, washed with brine and dried over $Na_2SO_4$. Removal of solvent gave the product as a white solid 2b. $^1$H-NMR (400 MHz, $CDCl_3$): δ 8.01 (1H, s), 7.62-7.64 (1H, d), 7.36-7.38 (1H, d), 7.17-7.21 (1H, td), 7.09-7.13 (1H, td), 6.95-6.96 (1H, d), 4.18-4.30 (2H, m), 2.85-3.20 (3H, m), 2.02-2.06 (2H, d), 1.65-1.68 (2H, m), 1.53 (9H, s); LC/MS: $C_{18}H_{24}N_2O_2$: m/z 300.7 (M+1).

B. 4-[1-(Toluene-4-sulfonyl)-1H-indol-3-yl]-piperidine-1-carboxylic acid tert-butyl ester. To a suspension of 2b (5 mmol) in toluene (15 mL) was added tetrabutylammonium hydrogensulfate (TBAHS) (0.26 g, 0.75 mmol), 50% aqueous NaOH solution (15 mL) and p-toluenesulfonyl chloride (TsCl) (1.43 g, 7.5 mmol) in that order. The mixture was stirred vigorously at rt for 16 h. After separation, the aqueous phase was extracted with EtOAc. The combined organic phases were washed with 1N HCl, saturated $NaHCO_3$, brine and dried over $Na_2SO_4$. The crude product was purified by column chromatography (eluent: EtOAc/hexanes, 3/7) to give 2c. $^1$H-NMR (400 MHz, $CDCl_3$): δ 7.97-7.99 (1H, d), 7.72-7.74 (2H, d), 7.50-7.52 (1H, d), 7.20-7.32 (5H, m), 4.18-4.30 (2H, m), 2.83-2.89 (3H, m), 2.33 (3H, s), 1.97-2.00 (2H, d), 1.56-1.66 (2H, qd), 1.49 (9H, s); LC/MS: $C_{25}H_{30}N_2O_4S$: m/z 455.2 (M+1).

C. 3-Piperidin-4-yl-1-(toluene-4-sulfonyl)-1H-indole. To a solution of 2c (1.98 g, 4.3 mmol) in DCM (10 mL) was added TFA (6 mL) and the mixture stirred at rt for 3 h. After removal of volatiles, the residue was dissolved in EtOAc, washed with saturated $NaHCO_3$, brine and dried over $Na_2SO_4$. Removal of solvent and evaporation to dryness gave the product 2d as a white foam. $^1$H-NMR (400 MHz, $CDCl_3$): δ 7.98-8.00 (1H, d), 7.73-7.76 (2H, m), 7.51-7.53 (1H, d), 7.29-7.33 (2H, m), 7.20-7.24 (3H, m), 3.79 (1H, s), 3.29-3.32 (2H, d), 2.85-2.94 (3H, m), 2.33 (3H, s), 2.04-2.08 (2H, d), 1.72-1.83 (2H, qd); LC/MS: $C_{20}H_{22}N_2O_2S$: m/z 355.2 (M+1).

D. 3-(1-Nitroso-piperidin-4-yl)-1-(toluene-4-sulfonyl)-1H-indole. To a solution of 2d (1.62 g, 4.57 mmol) in $CHCl_3$ (20 mL) was added 5M aqueous HCl solution (4.34 mL) and $NaNO_2$ (1.58 g, 22.9 mmol) in portions. After completion of addition, the mixture was stirred vigorously at rt overnight. The organic phase was separated and the aqueous phase was washed with CHCl3. The combined organic phases were washed with saturated $NaHCO_3$ solution, brine, and dried over $Na_2SO_4$. Removal of solvent gave the product 2e as a yellow foam. $^1$H-NMR (400 MHz, $CDCl_3$): δ 7.99-8.01 (1H, d), 7.73-7.76 (2H, m), 7.50-7.52 (1H, m), 7.31-7.36 (2H, m), 7.21-7.27 (3H, m), 5.15-5.20 (1H, m), 4.89-4.94 (1H, m), 3.81-3.89 (1H, dt), 3.11-3.18 (1H, tt), 2.68-2.75 (1H, td), 2.28-2.37 (4H, m), 2.09-2.15 (1H, m), 1.83-1.94 (1H, qd), 1.50-1.61 (1H, qd); LC/MS: $C_{20}H_{21}N_3O_3S$: m/z 384.1 (M+1).

E. 4-(1H-Indol-3-yl)-piperidin-1-ylamine. To 1M lithium aluminum hydride solution in THF (5.5 mL, 5.5 mmol) was added a solution of 2e (1.5 g, 3.9 mmol) in THF (10 mL) dropwise at 0° C. After completion of addition, the mixture was stirred at rt for 30 min, and refluxed under Ar overnight. The mixture was then hydrolyzed by careful addition of EtOH (ethanol, 1 mL) and $H_2O$ (3 mL) and filtered. The solution was washed with EtOAc. The collected filtrate was washed with 2N NaOH and brine, and dried over $Na_2SO_4$. Removal of solvent and evaporation to dryness gave the product 2f. $^1$H-NMR (400 MHz, $CD_3OD$): δ 7.55-7.57 (1H, d), 7.30-7.32 (1H, d), 6.95-7.08 (3H, m), 3.21-3.24 (2H, d), 2.81-2.84 (1H, m), 2.40-2.45 (2H, t), 2.01-2.09 (2H, m), 1.84-1.94 (2H, m); LC/MS: $C_{13}H_{17}N_3$: m/z 216.2 (M+1).

Example 3

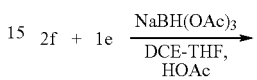

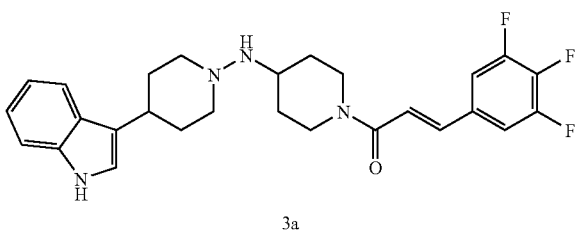

A. 1-{4-[4-(1H-Indol-3-yl)-piperidin-1-ylamino]-piperidin-1-yl}-3-(3,4,5-trifluoro-phenyl)-propenone. A suspension of 2f (0.65 g, 3 mmol) and 1e (0.85 mmol) in DCE (8 mL) and THF (2 mL) was treated with HOAc (acetic acid) (0.26 mL, 4.5 mmol) and $NaBH(OAc)_3$ (sodium triacetoxy borohydride) (0.95 g, 4.5 mmol) and the mixture was stirred at rt overnight. After removal of solvent, the residue was purified by column chromatography (eluent: EtOAc/hexanes, 4/5) to give 3a. $^1$H-NMR (400 MHz, DMSO-$d_6$): δ 10.75 (1H, s), 7.79-7.83 (2H, dd), 7.52-7.54 (1H, d), 7.31-7.39 (3H, m), 7.03-7.09 (2H, m), 6.93-6.97 (1H, m), 4.06-4.08 (2H, m), 2.9-3.18 (5H, m), 2.65-2.78 (1H, m), 2.27-2.33 (2H, m), 1.92-1.95 (2H, m), 1.70-1.81 (4H, m), 1.20-1.38 (2H, m); LC/MS: $C_{27}H_{29}F_3N_4O$: m/z 483.2 (M+1).

Example 4

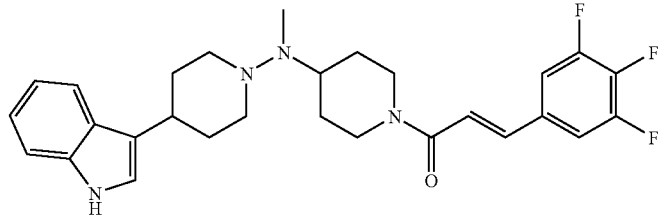

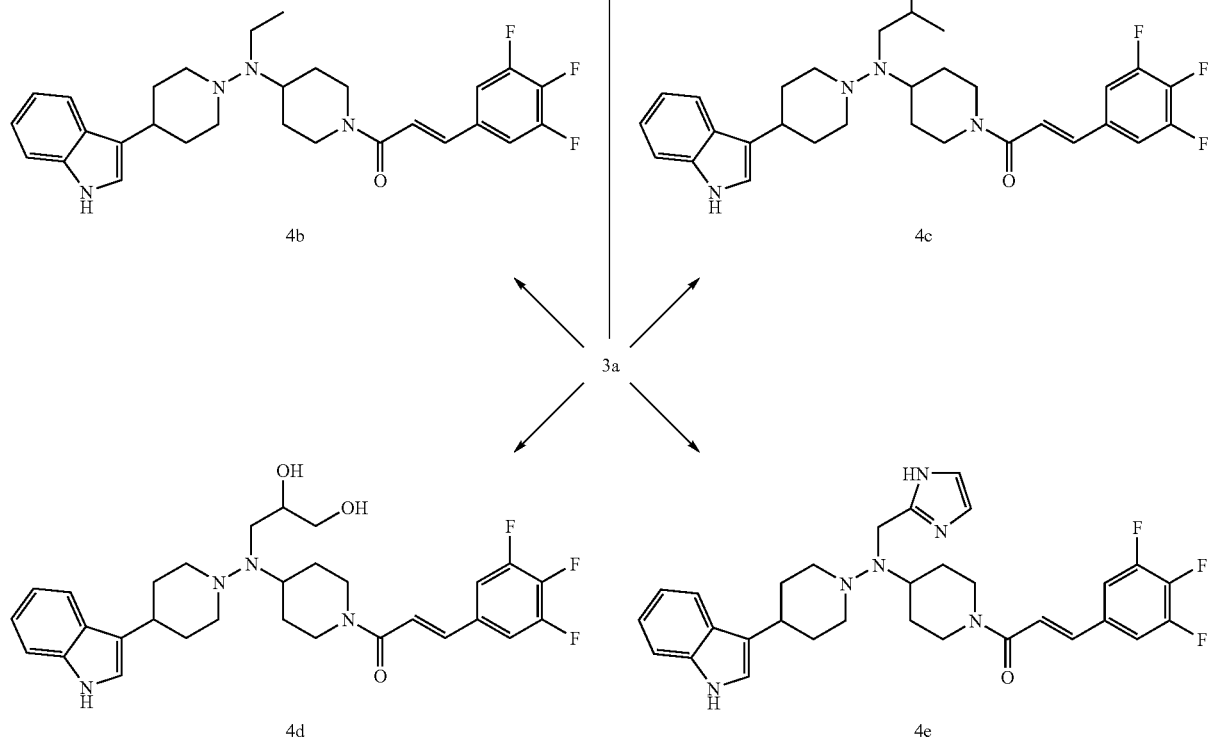

A. 1-(4-{[4-(1H-Indol-3-yl)-piperidin-1-yl]-methylamino}-piperidin-1-yl)-3-(3,4,5-trifluoro-phenyl)-propenone. A mixture of compound 3a (0.05 g, 0.1 mmol), formaldehyde (37% in $H_2O$, 0.48 g, 0.6 mmol) and $NaBH(OAc)_3$ (0.15 g, 0.7 mmol) in DCE (2 mL), HOAc (0.1 mL) and THF (1 mL) was stirred at rt for 3 days. Aqueous work-up and HPLC purification, followed neutralization by $NaHCO_3$ solution, gave 4a as a yellow solid. $^1$H-NMR (400 MHz, $CDCl_3$): δ 8.13 (1H, s), 7.62-7.64 (1H, d), 7.45-7.49 (1H, d), 7.35-7.37 (1H, d), 7.08-7.20 (4H, m), 6.95-6.96 (1H, d),6.83-6.87 (1H, d), 4.27-4.34 (1H, d), 3.92-3.95 (1H, d), 3.27-3.32 (1H, t), 3.14-3.19 (1H, t), 2.91-2.94 (2H, d), 2.58-2.78 (4H, m), 2.39 (3H, s), 1.94-2.08 (3H, m), 1.74-1.83 (3H, m), 1.55-1.66 (2H, m); LC/MS: $C_{28}H_{31}F_3N_4O$: m/z 497.3 (M+1).

B. 1-(4-{Ethyl-[4-(1H-indol-3-yl)-piperidin-1-yl]-amino}-piperidin-1-yl)-3-(3,4,5-trifluoro-phenyl)-propenone. The compound 4b was prepared in accordance with the procedure A in Example 4 by using acetaldehyde instead of formaldehyde. $^1$H-NMR (400 MHz, $CDCl_3$): δ 8.10 (1H, s), 7.61-7.63 (1H, d), 7.45-7.49 (1H, d), 7.34-7.36 (1H, d), 7.07-7.19 (4H, m), 6.95-6.96 (1H, d), 6.83-6.87 (1H, d), 4.47-4.50 (1H, d), 4.10-4.15 (2H, q), 4.01-4.04 (1H, d), 3.89-3.96 (1H, m), 3.20-3.26 (1H, t), 2.70-2.98 (6H, m), 2.01-2.04 (2H, d), 1.65-1.89 (6H, m), 1.12-1.16 (3H, t); LC/MS: $C_{29}H_{33}F_3N_4O$: m/z 511.3 (M+1).

C. 1-(4-{[4-(1H-Indol-3-yl)-piperidin-1-yl]-isobutylamino}-piperidin-1-yl)-3-(3,4,5-trifluoro-phenyl)-propenone. The compound 4c was prepared in accordance with the procedure A in Example 4 by using 2-methyl-propionaldehyde instead of formaldehyde. $^1$H-NMR (400 MHz, $CDCl_3$): δ 8.04 (1H, s), 7.60-7.62 (1H, d), 7.47-7.50 (1H, d), 7.34-7.36 (1H, d), 7.07-7.19 (4H, m), 6.95-6.96 (1H, d), 6.84-6.88 (1H, d), 4.60-4.64 (1H, d), 4.05-4.09 (1H, q), 3.14-3.20 (1H, t), 2.92-2.98 (2H, m), 2.63-2.83 (6H, m), 2.45-2.48 (2H, dd), 1.99-2.05 (3H, m), 1.66-1.88 (5H, m), 0.92-0.93 (6H, d); LC/MS: $C_{31}H_{37}F_3N_4O$: m/z 539.3 (M+1).

D. 1-(4-{(2,3-Dihydroxy-propyl)-[4-(1H-indol-3-yl)-piperidin-1-yl]-amino}-piperidin-1-yl)-3-(3,4,5-trifluorophenyl)-propenone. The compound 4d was prepared in accordance with the procedure A in Example 4 by using 2,3-dihydro-propionaldehyde instead of formaldehyde. $^1$H-NMR (400 MHz, $CD_3OD$): δ 8.04 (1H, s), 7.41-7.54 (4H, m), 7.30-7.32 (1H, d), 7.20-7.23 (1H, d), 7.04-7.08 (1H, m), 6.94-6.98 (2H, m), 4.60-4.64 (1H, d), 4.27-4.31 (1H, d), 3.77-3.82 (2H, m), 3.54-3.64 (2H, m), 3.15-3.28 (3H, m), 2.73-2.89 (6H, m), 2.08-2.14 (2H, d), 1.86-1.95 (2H, m), 1.73-1.83 (2H, m), 1.53-1.64 (2H, m); LC/MS: $C_{30}H_{35}F_3N_4O_3$: m/z 557.0 (M+1).

E. 1-(4-{(1H-Imidazol-2-ylmethyl)-[4-(1H-indol-3-yl)-piperidin-1-yl]-amino}-piperdin-1-yl)-3-(3,4,5-trifluoro-phenyl)-propenone. The compound 4e was prepared in accordance with the procedure A in Example 4 by using 1H-imidazole-2-carbaldehyde instead of formaldehyde. $^1$H-NMR (400 MHz, $CD_3OD$): δ 7.39-7.52 (4H, m), 7.29-7.31 (1H, d), 7.18-7.21 (1H, d), 7.02-7.07 (3H, m), 6.93-6.97 (2H, m) 4.39-4.43 (1H, d), 4.15-4.19 (1H, d), 4.07-4.10 (3H, m), 3.21-3.30 (1H, t), 3.10-3.13 (2h, d), 2.86-2.94 (2H, m), 2.63-2.71 (3H, m), 1.93-2.03 (3H, m), 1.78-1.84 (2H, m), 1.53-159 (2H, m); LC/MS: $C_{31}H_{33}F_3N_6O$: m/z 563.3 (M+1).

Example 5

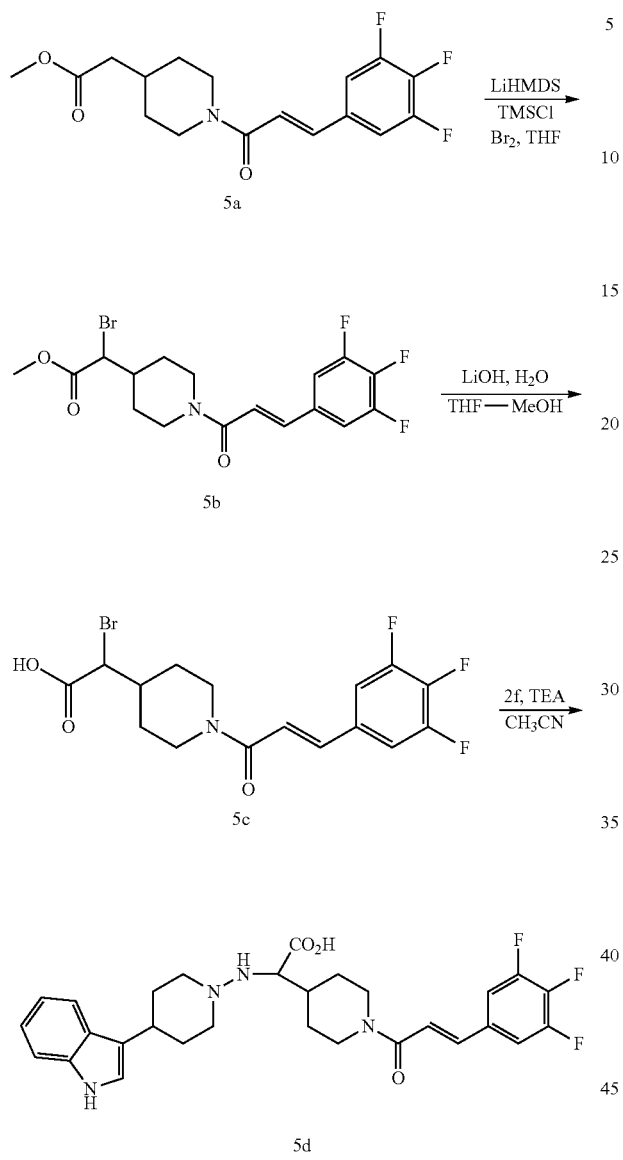

A. Bromo-{1-[3-(3,4,5-trifluoro-phenyl)-acryloyl]-piperidin-4-yl}-acetic acid methyl ester. Into a cooled (−78° C.) solution of LiHMDS (1.0 M in THF) was added a solution of 5a prepared according to the procedure from Xia, Mingde; Wachter, Michael P.; Pan, Meng; Demong, Duane E.; Pollack, Scott K., U.S. Pat. Appl. Publ. (2005), US2006069123, pp76) (6.83 g, 20 mmol) in THF (70 mL) dropwise in 30 min. After stirring at −78° C. for 1 h, TMS-Cl (5.06 mL, 60 mmol) was added dropwise. The solution was stirred at −78° C. for another 2 h and quenched by the dropwise addition of bromine (1.03 mL, 20 mmol) in THF (10 mL). The reaction mixture was then poured into a solution of EtOAc (150 mL) and saturated NaHCO$_3$ solution (150 mL). The two phases were separated and the aqueous phase was extracted with EtOAc. The combined organic phases were washed with brine, and dried over Na$_2$SO$_4$. Removal of solvent by evaporation and purification by column chromatography (eluent: EtOAc/hexanes, 3/7) gave compound 5b. $^1$H-NMR (400 MHz, CDCl$_3$): δ 7.47-7.51 (1H, d), 7.11-7.15 (2H, t), 6.79-6.83 (1H, d), 4.74-4.81 (1H, m), 4.05-4.07 (1H, d), 3.80 (3H, s), 3.10-3.20 (1H, m), 2.66-2.72 (1H, m), 2.16-2.24 (2H, m), 1.72-1.79 (2H, m), 1.26-1.36 (2H, m); LC/MS: C$_{17}$H$_{17}$Br F$_3$NO$_3$: m/z 420.0 (M+1).

B. Bromo-{1-[3-(3,4,5-trifluoro-phenyl)-acryloyl]-piperidin-4-yl}-acetic acid. To a stirred solution of 5b (0.7 g, 1.67 mmol) in MeOH (13 mL) and THF (4.4 mL) was added a solution of LiOH (0.2 g, 8.35 mmol) in H$_2$O (4.4 mL) dropwise. The mixture was stirred at rt until thin layer chromatography (tlc) showed no starting material left. The volatiles were removed by evaporation and the solid was filtered, washed with H$_2$O, dried in vacuum to give 5c as a white solid. $^1$H-NMR (400 MHz, DMSO-d$_6$): δ 13.4 (1H, s), 7.79-7.83 (2H, t), 7.33-7.44 (2H, m), 4.47-4.54 (1H, t), 4.33-4.35 (1H, d), 3.08-3.13 (1H, m), 2.66-2.73 (1H, m), 2.09-2.12 (1H, m), 1.91-1.99 (1H, m), 1.68-1.75 (2H, m), 1.16-1.29 (2H, m); LC/MS: C$_{16}$H$_{15}$Br F$_3$NO$_3$: m/z 406.0 (M+1).

C. [4-(1H-Indol-3-yl)-piperidin-1-ylamino]-{1-[3-(3,4,5-trifluoro-phenyl)-acryloyl]-piperidin-4-yl}-acetic acid. A mixture of 2f (0.012 g, 0.054 mmol), 5c (0.02 g, 0.049 mmol) and TEA (0.01 mL, 0.065 mmol) in CH$_3$CN (1 mL) was heated at reflux for 5 h. Removal of the solvent and purification by HPLC gave racemate 5d as a THF salt. $^1$H-NMR (400 MHz, CD$_3$OD): δ 7.39; LC/MS: C$_{29}$H$_{31}$F$_3$N$_4$O$_3$: m/z 541.3 (M+1).

IN VITRO BIOLOGICAL DATA

Compounds of the invention were subjected to various representative biological tests.

The results of these tests are intended to illustrate the invention in a non-limiting fashion.

MCP-1 Receptor Binding Assay in THP-1 Cells

Human monocytic cell line THP-1 cells were obtained from American Type Culture Collection (Manassas, Va., USA). The THP-1 cells were grown in RPMI-1640 (RPMI: Roswell Park Memorial Institute Medium-cell culture growth media) supplemented with 10% fetal bovine serum in a humidified 5% CO$_2$ atmosphere at 37° C. The cell density was maintained between 0.5×10$^6$ cells/mL.

THP-1 (cells were incubated with 0.5 nM $^{125}$I labeled MCP-1 (Perkin-Elmer Life Sciences, Inc. Boston, Mass.) in the presence of varying concentrations of either unlabeled MCP-1 (R & D Systems, Minneapolis, Minn.) or test compound for 2 hours at 30° C. in a 96 well plate. Cells were then harvested onto a filter plate, dried, and 20 μL of Microscint 20 was added to each well. Plates were counted in a TopCount NXT, Microplate Scintillation & Luminescence Counter (Perkin-Elmer Life Sciences, Inc. Boston, Mass.). Blank values (buffer only) were subtracted from all values and drug treated values were compared to vehicle treated values. 1 μM cold MCP-1 was used for nonspecific binding.

Table 1 lists IC$_{50}$ values for inhibition of MCP-1 binding to CCR2 obtained for test compounds of the invention. Where an IC$_{50}$ value was not obtained for a particular compound, the percent inhibition is provided at a test concentration of 25 μM. TABLE 1 Inhibition of MCP-1 Binding IC$_{50}$ (μM)

TABLE 1

Inhibition of MCP-1 Binding

| Structure | Name | IC$_{50}$ (μM) | Inh (%) |
|---|---|---|---|
| 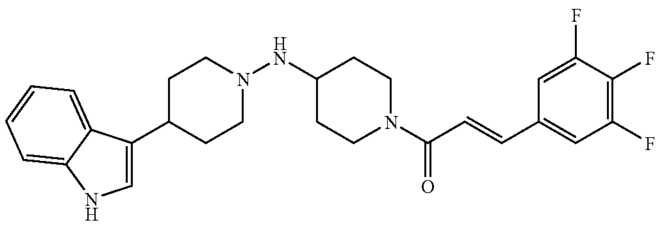 | 1-{4-[4-(1H-Indol-3-yl)-piperidin-1-ylamino]-piperidin-1-yl}-3-(3,4,5-trifluoro-phenyl)-propenone | 1.6 | |
| 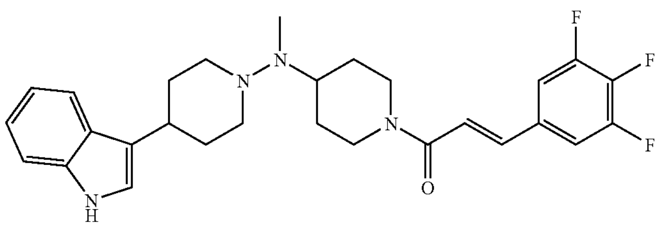 | 1-(4-{[4-(1H-Indol-3-yl)-piperidin-1-yl]-methyl-amino}-piperidin-1-yl)-3-(3,4,5-trifluoro-phenyl)-propenone | | 59 |
| 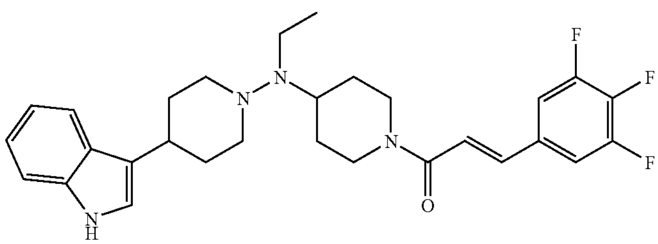 | 1-(4-{Ethyl-[4-(1H-indol-3-yl)-piperidin-1-yl]-amino}-piperidin-1-yl)-3-(3,4,5-trifluoro-phenyl)-propenone | | 34 |
| 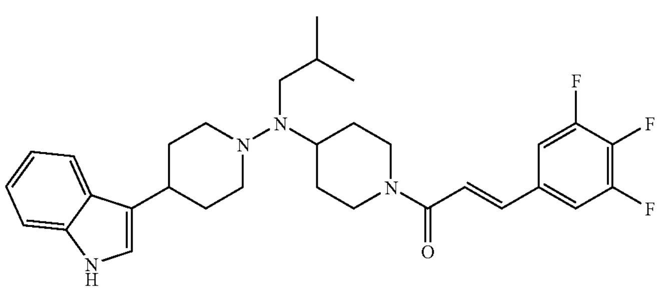 | 1-(4-{[4-(1H-Indol-3-yl)-piperidin-1-yl]-isobutyl-amino}-piperidin-1-yl)-3-(3,4,5-trifluoro-phenyl)-propenone | | 0 |
| 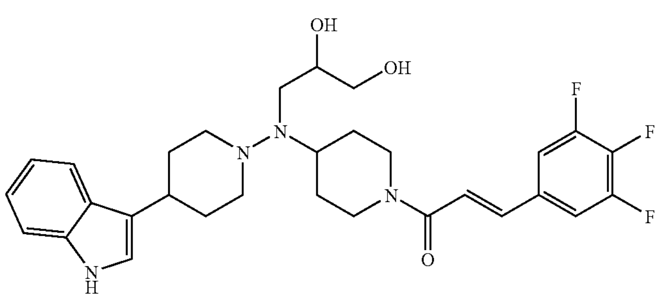 | 1-(4-{(2,3-Dihydroxy-propyl)-[4-(1H-indol-3-yl)-piperidin-1-yl]-amino}-piperidin-1-yl)-3-(3,4,5-trifluoro-phenyl)-propenone | 1 | |

TABLE 1-continued

Inhibition of MCP-1 Binding

| Structure | Name | IC$_{50}$ (µM) | Inh (%) |
|---|---|---|---|
| 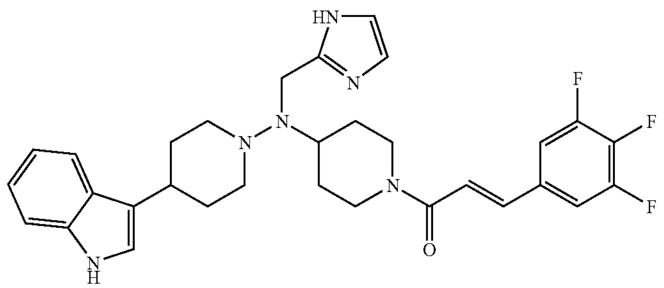 | 1-(4-{(1H-Imidazol-2-ylmethyl)-[4-(1H-indol-3-yl)piperidin-1-yl]-amino}-piperidin-1-yl)-3-(3,4,5-trifluoro-phenyl)-propenone | | 20 |
| 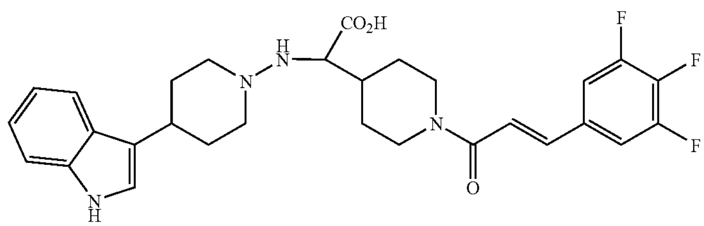 | [4-(1H-Indol-3-yl)-piperidin-1-ylamino]-{1-[3-(3,4,5-trifluoro-phenyl)-acryloyl]-piperidin-4-yl}-acetic acid | 0.64 | |

MCP-1 Induced Calcium Mobilization in THP-1 Cells

THP-1 cells are plated at a density of $8 \times 10^5$ cells/mL (100 µL/well) into poly-D lysine coated clear bottom, black 96 well plates. The cells are loaded with 5 µM fluo-3 for 45 minutes. The fluo-3 is washed off and cells are incubated with varying concentrations of test compound for 15 minutes. The change in calcium ion concentration upon addition of 0.2 µM MCP-1 is determined using FLIPR and compared to vehicle.

MCP-1 Induced Chemotaxis in THP-1 Cells

MCP-1 induced chemotaxis is run in a 24-well chemotaxis chamber. MCP-1 (0.1 µg/mL) is added to the lower chamber and 100 µL of THP-1 cells ($1 \times 10^7$ cell/mL) is added to the top chamber. varying concentrations of test compound are added to the top and bottom chambers. cells are allowed to chemotaxis for 3 hours at 37° C. and 5% $CO_2$. An aliquot of the cells that migrate to the bottom chamber are taken and counted then compared to vehicle.

Collagen-Induced Arthritis Model

In a collagen-induced arthristis model I mice, DBA1 mice are immunized with bovine type II collagen on day 0, injected (sc) with lipopolysaccharide (LPS) on day 21, and dosed (ip, bid) with a test compound at either 25, 50 or 100 mg/kg from day 20 to day 35. Body weight is monitored, and clinical disease score recorded every 2-3 days starting on day 20.

Inhibition of Ovalbumin-Induced Allergic Rhinitis in Mice

BALB/c mice are sensitized by i.p. injection of ovalbumin (OVA) emulsified in alum (Day 0, 5, 14, 21). (Groups of mice are each challenged by intranasal injection of OVA (Day 22-35, 38). Control group mice receive an equal volume of vehicle by intranasal injection. Nasal symptoms (number of sneezes and episodes of nose rubbing by the front paws) are counted during the 5 min period following the last intranasal injection (Day 38).

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula I,

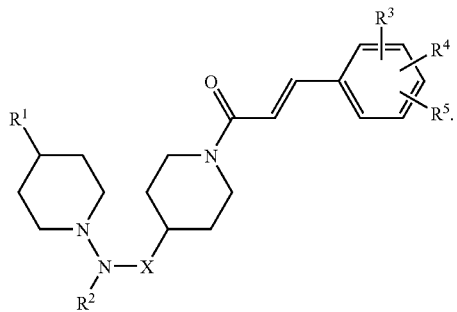

I wherein:
$R^1$ is phenyl, naphthyl, heteroaryl, or partially saturated benzofused heteroaryl, wherein the phenyl, naphthyl, heteroaryl, or partially saturated benzofused heteroaryl may be optionally substituted with up to three substituents selected from the group consisting of —F, —Cl, —CF$_3$, —CN, —C$_{(1-4)}$alkyl, —C$_{(1-4)}$alkylOH, —C$_{(1-4)}$alkylNH$_2$, —C$_{(1-4)}$alkylNHC$_{(1-4)}$alkyl, —C$_{(1-4)}$alkylN(C$_{(1-4)}$alkyl)$_2$, —NO$_2$, —NHC$_{(1-4)}$alkyl, —CONHC$_{(1-4)}$alkyl, —SO$_2$NHC$_{(1-4)}$alkyl, —OC$_{(1-4)}$alkyl, —NH$_2$, —CONH$_2$, —SO$_2$NH$_2$, —NHCOCH$_3$, and —OH;

$R^2$ is H, —C$_{(1-4)}$alkyl, or —C$_{(1-4)}$alkyl-OH, wherein said —C$_{(1-4)}$alkyl and said —C$_{(1-4)}$alkyl-OH are optionally substituted with —OH, —NH$_2$, —F, —Cl, heteroaryl, or phenyl;

X is a direct bond, or CHCO$_2$H;

$R^3$ is —F, —Cl, —CF$_3$, —CN, —C$_{(1-4)}$alkyl, —C$_{(1-4)}$alkylOH, —C$_{(1-4)}$alkylNH$_2$, —C$_{(1-4)}$alkylNHC$_{(1-4)}$alkyl, —C$_{(1-4)}$alkylN(C$_{(1-4)}$alkyl)$_2$, —NO$_2$, —NHC$_{(1-4)}$alkyl, —CONHC$_{(1-4)}$alkyl, —SO$_2$NHC$_{(1-4)}$alkyl, —OC$_{(1-4)}$alkyl, —NH$_2$, —CONH$_2$, —SO$_2$NH$_2$, —NHCOCH$_3$, or —OH;

R[4] is —F, —Cl, —OCH$_3$, or may be taken together with an adjacent R[3] to form a methylidene acetal; and R[5] is —F, Cl, or —OCH$_3$;

and pharmaceutically acceptable salts thereof.

2. A compound of claim 1, wherein:

R[1] is

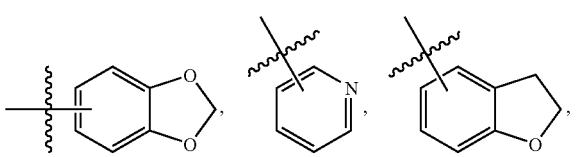

or indolyl, any of which may be optionally substituted with up to three substituents selected from the group consisting of —F, —Cl, —CF$_3$, —CN, —C$_{(1-4)}$alkyl, —C$_{(1-4)}$alkylOH, —C$_{(1-4)}$alkylNH$_2$, —C$_{(1-4)}$alkyl NHC$_{(1-4)}$alkyl, —C$_{(1-4)}$alkylN(C$_{(1-4)}$alkyl)$_2$, —NO$_2$, —NHC$_{(1-4)}$alkyl, —CONHC$_{(1-4)}$alkyl, —SO$_2$NHC$_{(1-4)}$alkyl, —OC$_{(1-4)}$alkyl, —NH$_2$, —CONH$_2$, —SO$_2$NH$_2$, —NHCOCH$_3$, and —OH;

R[2] is H,

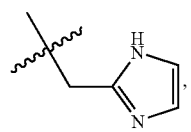

—C$_{(1-4)}$alkyl, or —C$_{(1-4)}$alkyl-OH, wherein said —C$_{(1-4)}$alkyl and said —C$_{(1-4)}$alkyl-OH are optionally substituted with —OH, —NH$_2$, —F, —Cl, or phenyl; and R[3] is —F, —Cl, —CF$_3$, —CN, —C$_{(1-4)}$alkyl, —C$_{(1-4)}$alkylOH, —C$_{(1-4)}$alkylNH$_2$, —C$_{(1-4)}$alkylNHC$_{(1-4)}$alkyl, —C$_{(1-4)}$alkylN(C$_{(1-4)}$alkyl)$_2$, —NO$_2$, —NHC$_{(1-4)}$alkyl, —OC$_{(1-4)}$alkyl, —NH$_2$, —OH;

and pharmaceutically acceptable salts thereof.

3. A compound of claim 2, wherein:

R[1] is

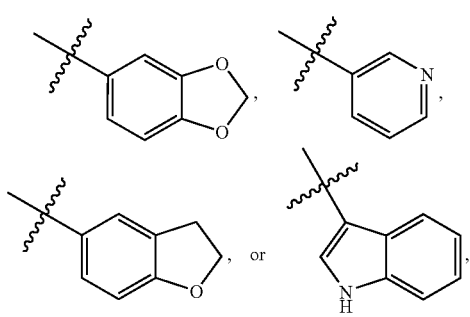

any of which may be optionally substituted with up to three substituents selected from the group consisting of —F, —Cl, —CF$_3$, —CN, —OH, —OC$_{(1-4)}$alkyl, —C$_{(1-4)}$alkyl, and —C$_{(1-4)}$alkylOH;

R[2] is H,

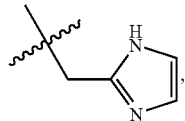

—C$_{(1-4)}$alkyl, or —C$_{(1-4)}$alkyl-OH, wherein said —C$_{(1-4)}$alkyl and said —C$_{(1-4)}$alkyl-OH are optionally substituted with —OH, —NH$_2$, —F, or —Cl;

R[3] is —F, Cl, or —OCH$_3$;

and pharmaceutically acceptable salts thereof.

4. A compound of claim 3, wherein:

R[1] is

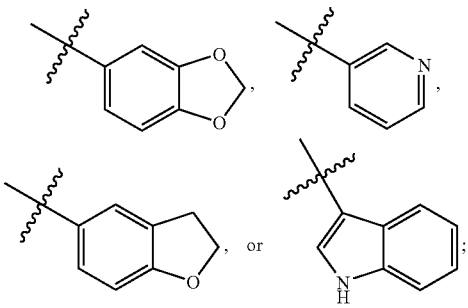

R[2] is H,

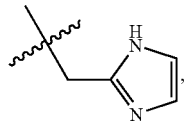

—C$_{(1-4)}$alkyl, or —C$_{(1-4)}$alkyl-OH, wherein said —C$_{(1-4)}$alkyl-OH is optionally substituted with —OH; and R[4] is —F, Cl, or —OCH$_3$;

and pharmaceutically acceptable salts thereof.

5. A compound of claim 4, wherein:

R[1] is

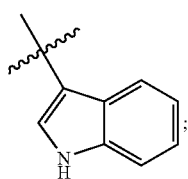

R[2] is H, C$_{(1-4)}$alkyl, dihydroxypropyl, or

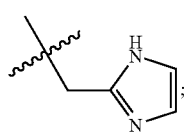

R[3] is F;
R[4] is F; and
R[5] is F;

and pharmaceutically acceptable salts thereof.

6. A compound selected from the group consisting of:

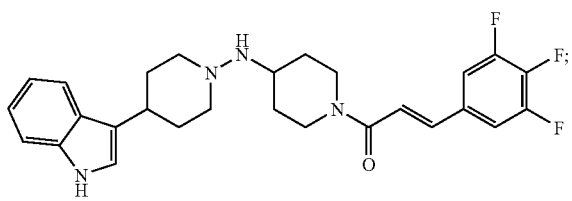

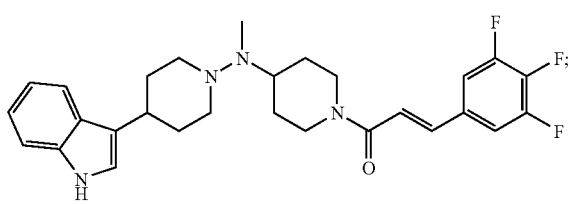

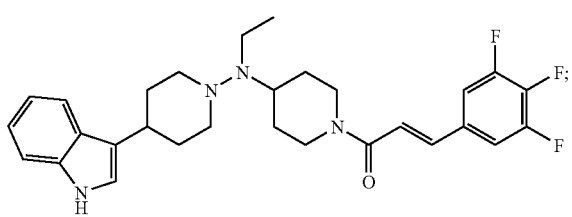

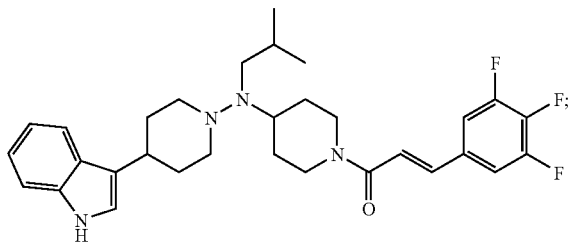

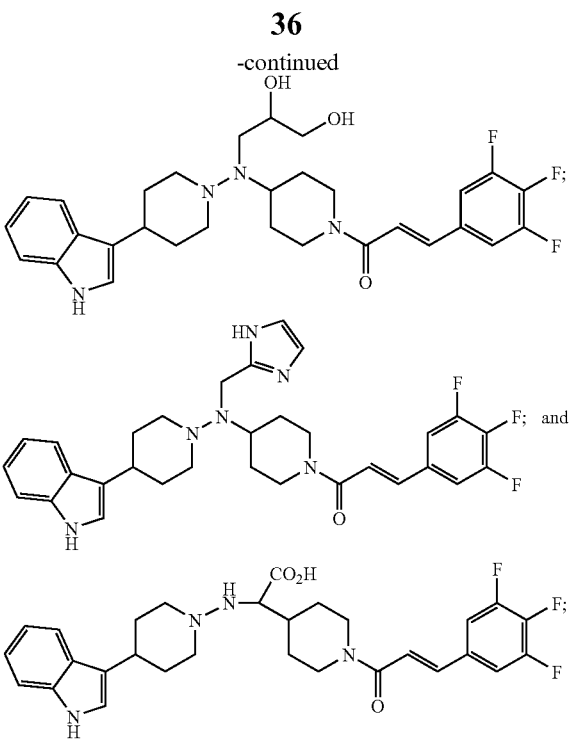

pharmaceutically acceptable salts thereof.

7. A pharmaceutical composition, comprising a compound of claim 1 and a pharmaceutically acceptable carrier.

8. A pharmaceutical composition made by mixing a compound of claim 1 and a pharmaceutically acceptable carrier.

9. A process for making a pharmaceutical composition comprising mixing a compound of claim 1 and a pharmaceutically acceptable carrier.

* * * * *